United States Patent
Aust et al.

(10) Patent No.: US 6,696,602 B1
(45) Date of Patent: Feb. 24, 2004

(54) METHOD FOR THE PRODUCTION OF PHOSPHONOMETHYLGLYCINE

(75) Inventors: Nicola Christiane Aust, Büren (DE); Thomas Butz, Mannheim (DE); Martin Fischer, Ludwigshafen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 99 days.

(21) Appl. No.: 10/048,838

(22) PCT Filed: Aug. 10, 2000

(86) PCT No.: PCT/EP00/07809

§ 371 (c)(1),
(2), (4) Date: Feb. 6, 2002

(87) PCT Pub. No.: WO01/12640

PCT Pub. Date: Feb. 22, 2001

(30) Foreign Application Priority Data

Aug. 11, 1999 (DE) .......................... 199 37 959

(51) Int. Cl.⁷ .................................. C07F 9/28
(52) U.S. Cl. ................ 562/17; 562/8; 562/11; 502/216; 423/336
(58) Field of Search ................. 562/8, 11, 17, 562/23, 512

(56) References Cited

U.S. PATENT DOCUMENTS

| | | | |
|---|---|---|---|
| 3,950,402 A | 4/1976 | Franz | 260/502 |
| 3,954,848 A | 5/1976 | Franz | 260/502 |
| 5,023,369 A | 6/1991 | Fields, Jr. | 562/17 |
| 5,047,579 A | 9/1991 | Glowka et al. | 562/17 |
| 5,095,140 A | 3/1992 | Fields, Jr. | 562/17 |

FOREIGN PATENT DOCUMENTS

| | | |
|---|---|---|
| BR | 9 601 581 | 7/1999 |
| HU | 187 341 | 2/1984 |

Primary Examiner—Johann Richter
Assistant Examiner—Karl Puttlitz
(74) Attorney, Agent, or Firm—Keil & Weinkauf

(57) ABSTRACT

The present invention relates to a process for the preparation of phosphonomethylglycine, wherein N-phosphonomethyliminodiacetic acid N-oxide is brought into contact with a catalytically effective amount of thiocyanic acid or a salt thereof.

11 Claims, 2 Drawing Sheets

METHOD FOR THE PRODUCTION OF PHOSPHONOMETHYLGLYCINE

FIELD OF THE INVENTION

The present invention relates to a process for the preparation of phosphonomethylglycine from N-phosphonomethyliminodiacetic acid N-oxide.

BACKGROUND OF THE INVENTION

Phosphonomethylglycine, which is known under the common name glyphosate, is a potent phytotoxic compound which is employed as herbicide.

EP-A-439445 describes the preparation of phosphonomethylglycine starting from N-phosphonomethyliminodiacetic acid. The latter is oxidized with a peroxide in aqueous solution, if appropriate in the presence of a catalytically effective amount of a water-soluble molybdenum compound, to give the intermediate N-phosphonomethyliminodiacetic acid N-oxide. The N-oxide is subsequently converted into phosphonomethylglycine in the presence of a catalytic amount of a metabisulfite compound and a water-soluble molybdenum compound.

EP-A-464017 also describes a process for the preparation of phosphonomethylglycine starting from phosphonomethyliminodiacetic acid using the same process steps. The oxidation to give the abovementioned N-oxide is carried out with a peroxide in the presence of a water-soluble molybdenum or tungsten compound. The conversion into phosphonomethylglycine is then carried out using iron, zinc, aluminum, vanadium or copper in the form of the metal or using a vanadium salt, iron(II) salt or copper(I) salt as catalyst.

Finally, EP-A-464018 also describes a process for the preparation of phosphonomethylglycine, the oxidation of the phosphonomethyliminodiacetic acid being carried out with a peroxide in the presence of a water-soluble tungsten compound or of a mixture of a water-soluble tungsten and molybdenum compound as catalyst. The N-oxide is then brought into contact with metallic iron, a water-soluble vanadium compound, an iron(II) salt or a mixture of a water-soluble sulfide, sulfite or bisulfite compound and a water-soluble molybdate compound and is converted into phosphonomethylglycine.

Thus, readily reducible catalysts are employed when the N-oxide is converted into phosphonomethylglycine. Since peroxide is generally employed in an excess for oxidizing the N-phosphonomethylimino-diacetic acid, the result is a reaction between the excess peroxide and the readily oxidizable catalyst, which is thus inactivated, at least to some extent.

It is an object of the present invention to provide a process for the preparation of phosphonomethylglycine which rapidly yields phosphonomethylglycine in high yield and high selectivity, even in the presence of residual oxidant.

SUMMARY OF THE INVENTION

We have surprisingly found that this object is achieved when the oxidation of N-phosphonomethyliminodiacetic acid N-oxide is carried out with thiocyanic acid or a salt thereof as catalyst.

The present invention therefore relates to a process for the preparation of phosphonomethylglycine wherein N-phosphonomethyliminodiacetic acid N-oxide is brought into contact with a catalytically effective amount of thiocyanic acid or a salt thereof, if appropriate in the presence of a cocatalyst.

DETAILED DESCRIPTION OF THE INVENTION

Figure 1:
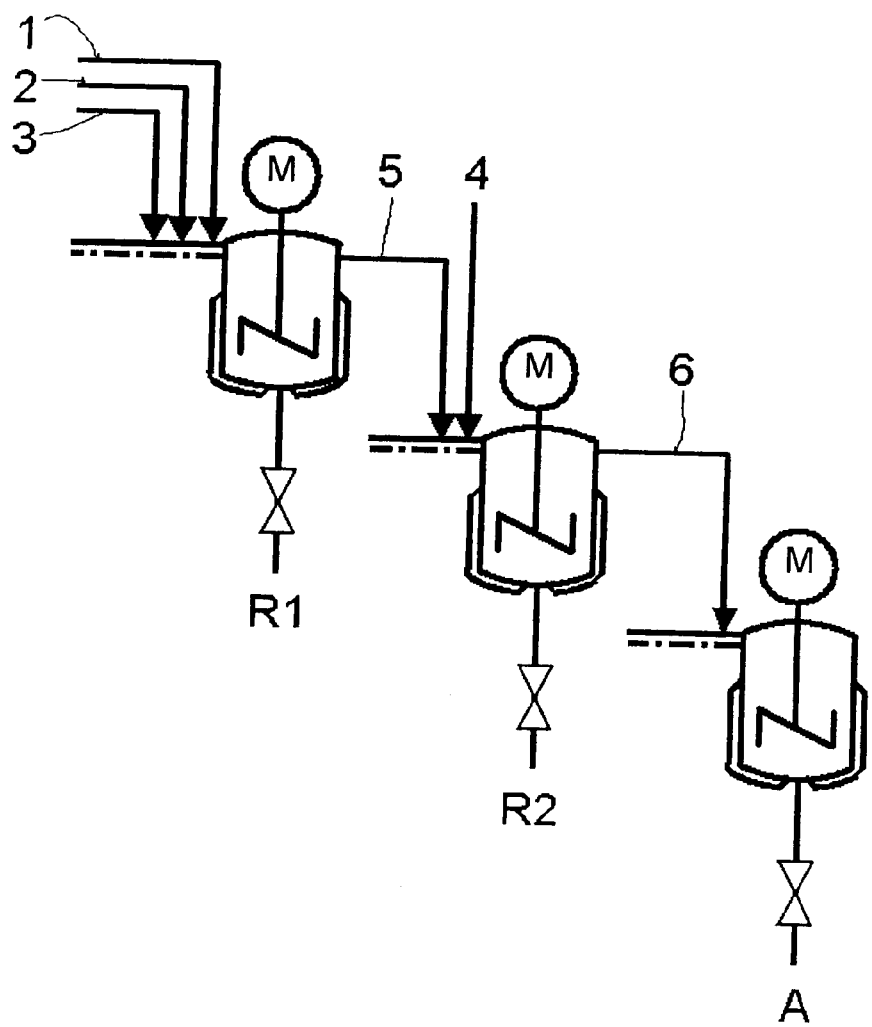
FIG. 1 is a schematic representation of apparatus for carrying out the process for the preparation of phosphonomethylglycine representing a cascade of two stirred reactors (R1 and R2) connected in series and a thermostatted discharge vessel A.

N-Phosphonomethyliminodiacetic acid N-oxide is known and can be prepared by a plurality of processes. In accordance with U.S. Pat. No. 3,950,402 or 3,954,848 or in accordance with HU 187,347, for example, it can be synthesized using peroxides in the presence of compounds of silver, iron, tin, lead, manganese or molybdenum. However, the N-oxide is preferably prepared by one of the processes described in the European Patent Applications EP 439445 A, EP 464017 A or EP 464018 A. Here, N-phosphonomethyliminodiacetic acid is brought into contact with a peroxide such as hydrogen peroxide, performic acid, peracetic acid, perbenzoic acid, peroxytrifluoroacetic acid, benzoyl peroxide, benzenepersulfonic acid and the like. It is preferred to use hydrogen peroxide, in particular in at least stoichiometric amounts based on N-phosphonomethyliminodiacetic acid. The hydrogen peroxide is generally employed in a concentration in the range of 10 to 70% by weight, in particular 30 to 70% by weight. The reaction temperature is generally in the range of approximately 0° C. to 80° C., in particular approximately 20° C. to approximately 70° C.

The oxidation of N-phosphonomethyliminodiacetic acid is particularly preferably carried out in the presence of a catalytic amount of a water-soluble molybdenum compound or a water-soluble tungsten compound or a mixture of these. Suitable molybdenum compounds are known to the skilled worker and all that is required is that they are soluble in the reaction medium.

Useful molybdenum compounds are, for example, alkali metal molybdates such as sodium molybdate, ammonium molybdate, or alkali metal polymolybdates or ammonium polymolybdates such as ammonium dimolybdate or sodium dimolybdate.

Suitable tungsten compounds too are known to the skilled worker, all that is required of them is that they are soluble in the reaction medium. Useful tungsten compounds are, for example, tungstic acid, 1,2-tungstophosphate and barium tungstate. Ammonium tungstate and alkali metal tungstates such as sodium tungstate and potassium tungstate are preferred.

The amount of catalyst can be varied within wide limits. In general, approximately 0.01 to approximately 5.0% by weight, preferably approximately 0.01 to approximately 3.0% by weight, of catalyst are used, based on the weight of N-phosphonomethyliminodiacetic acid.

The peroxide is generally applied in at least stoichiometric amounts. Preferably, a small excess, in particular approximately 1.02 to 1.20 molar equivalents, especially preferably 1.05 to 1.15 molar equivalents are used, based on the amount of phosphonomethyliminodiacetic acid.

The N-phosphonomethyliminodiacetic acid is oxidized in aqueous medium, the N-phosphonomethyliminodiacetic acid first being in the form of a suspension and dissolving during the course of the oxidation, at least to some extent. It is expedient to employ the N-phosphonomethyliminodiacetic acid in high concentration, for example in the form of an up to 60% by weight strength, in particular up to 50% by weight strength, aqueous suspension. It is preferred to employ the N-phosphonomethyliminodiacetic acid in such an amount that a solution is present when the oxidation has ended. The transition from the suspension to the solution indicates that the oxidation reaction is essentially complete since the N-oxide is considerably more readily soluble in water than the N-phosphonomethyliminodiacetic acid.

The N-oxide is preferably converted into the desired phosphonomethylglycine starting from an aqueous solution of the N-oxide. The catalyst used is thiocyanic acid or a salt thereof, which is preferably a water-soluble salt. The thiocyanic acid, which, at the reaction temperature, is in the form of a gas, can be employed in the form of an aqueous solution or as a gas, if appropriate diluted with an inert gas such as nitrogen. However, a salt of thiocyanic acid, in particular an alkali metal salt such as sodium thiocyanate or potassium thiocyanate is preferably used as catalyst. Again, the catalyst is preferably employed in the form of an aqueous solution.

The N-oxide is preferably converted into phosphonomethylglycine in the presence of a cocatalyst so as to increase the conversion rate. Examples of suitable cocatalysts are water-soluble cocatalysts such as vanadium salts, such as vanadyl sulfate, or water-soluble iron(II) salts such as iron (II) sulfate or iron(II) chloride. However, a water-soluble molybdenum compound such as ammonium molybdate or an alkali metal molybdate such as sodium molybdate or an ammonium polymolybdate or alkali metal polymolybdate such as ammonium dimolybdate or sodium dimolybdate is preferably used as cocatalyst. It is particularly preferred to use the same catalyst for oxidizing the N-phosphonomethyliminodiacetic acid and for the subsequent conversion of the N-oxide, in particular one of the abovementioned molybdenum compounds.

The amount of thiocyanic acid or a salt thereof is independent of the amount of peroxide employed for oxidizing the N-phosphonomethyliminodiacetic acid since the effect of the thiocyanic acid or the salts thereof is not adversely affected under the reaction conditions by any excess peroxide which may be present. In general, however, an amount of at least 0.01% by weight is used based on the amount of N-oxide. As a rule, not more than 10% by weight, preferably not more than 8% by weight, of catalyst is employed based on the N-oxide. The amount is preferably in the range of 0.01% by weight to approximately 6.0% by weight, in particular in the range of 0.1 to 5% by weight, based on the N-oxide.

The amount of cocatalyst is generally in the range of approximately 0.01 to approximately 30 mol %, preferably approximately 0.05 to approximately 10 mol %, based on the N-oxide. If the same catalyst is used for the preparation of the N-oxide and for its conversion into phosphonomethylglycine, in particular a water-soluble molybdenum compound, the catalyst is not removed from the reaction mixture after the oxidation has taken place so that addition of a cocatalyst for the subsequent conversion reaction can be dispensed with.

In general, the reaction temperature for converting the N-oxide into phosphonomethylglycine is in the range of 10° C. to 100° C., in particular 30° C. to 80° C., preferably 35° C. to 70° C. For the conversion reaction, the N-oxide can be brought into contact with the catalyst in the customary manner in a reaction chamber. However, the reaction is preferably carried out in such a way that an aqueous solution which contains at least some of the catalyst and, if appropriate, some of the N-oxide, for example up to 20% or up to 10%, is introduced and an aqueous solution of the N-oxide is metered in.

"Metering in" in the present context is to be understood as meaning that the N-oxide employed is introduced into the reaction chamber gradually, i.e. controlled in the course of time, and is there brought into contact with the catalyst in particular in the form of an aqueous solution. For example, this can be done by adding the N-oxide solution gradually or by introducing it portionwise in stages.

Some or all of the catalyst can be introduced first into the reaction chamber. If only some of the catalyst is introduced, the remainder may also be metered into the reaction chamber, either simultaneously with the N-oxide or staggered in time. Alternatively, all of the catalyst can be metered into the reaction chamber, again either simultaneously with the N-oxide or staggered in time.

When carrying out the reaction, however, it must always be ensured that at least 50%, preferably at least 70%, especially preferably at least 90%, of the N-oxide metered into the reaction chamber is converted. The conversion rate can be determined readily on the basis of the amount of carbon dioxide which is liberated during the reaction. Accordingly, the N-oxide is metered in such a way that at least 50%, preferably 70% and especially preferably 90% of the expected amount of carbon dioxide which is obtained during the conversion reaction and which corresponds to the amount of N-oxide which has already been added is liberated with only a short delay, in general not more than 15 minutes, before more N-oxide solution is added. As a rule, this is achieved by ensuring that at least 0.01 mol % of catalyst, based on the N-oxide which has already been metered in, is present in the reaction mixture. If, during the conversion reaction, carbon dioxide is evolved at a lower rate or ceases, more catalyst can be added to the reaction mixture or, if some of the catalyst is metered in, the latter can be metered in more rapidly.

The cocatalyst can be brought into contact with the N-oxide in the same manner as the catalyst.

During the conversion reaction, the phosphonomethylglycine precipitates as a solid when a concentration of approximately 1.0% by weight in the reaction mixture is exceeded. Accordingly, the reaction is expediently carried out in such a way that most of the phosphonomethylglycine is obtained as a solid. As a rule, this is the case when the N-oxide is employed in a concentration of at least 20% by weight based on the total weight of the reaction mixture.

The phosphonomethylglycine can be separated from the suspension obtained by the customary techniques of isolating solids. Before the separation, the mixture is expediently cooled to <30° C., in particular to 10 to 20° C., and/or stirred for 1 to 20 hours. At least some of the mother liquor which remains after the phosphonomethylglycine has been separated off and which still contains dissolved phosphonomethylglycine and the catalyst can be employed for the conversion of more N-oxide.

Both the preparation of the N-oxide and the subsequent conversion of the N-oxide into phosphonomethylglycine can be carried out as a batch, semi-batch (hydrogen peroxide, N-oxide solution and, if desired, some of the catalyst are metered in) or continuously (all components, i.e. N-phosphonomethyliminodiacetic acid, oxidant and, if appropriate, catalyst, or N-oxide, catalyst and, if appropriate, cocatalyst are metered in simultaneously).

The examples which follow illustrate the invention without imposing any limitation.

EXAMPLE 1

38 g of N-phosphonomethyliminodiacetic acid and 0.92 g of ammonium molybdate tetrahydrate are suspended in 100 ml of water and the suspension is warmed to 65° C. 20.6 g of 30% strength hydrogen peroxide solution are subsequently added dropwise in the course of 30 minutes and stirring is continued for one hour at 65° C., during which process a clear solution forms. 1.6 g of potassium thiocyanate, dissolved in 10 ml of water, are added dropwise at 40° C. to the N-oxide solution formed. A vigorous evolution of gas is observed. Stirring is continued for 1 hour at 40° C., and the precipitate which has separated out is subsequently filtered off and dried at room temperature. This procedure allows 20.9 g of N-phosphonomethylglycin to be isolated in a purity of 98%. This corresponds to a yield of 72% based on the amount of N-phosphonomethyliminodiacetic acid employed.

EXAMPLE 2

60 g of N-phosphonomethyliminodiacetic acid and 1.23 g of ammonium molybdate tetrahydrate are suspended in 75 ml of water and the suspension is warmed to 55° C. 19.8 g of 50% strength hydrogen peroxide solution is subsequently added dropwise in the course of 15 minutes and stirring is continued for 1.5 hours at 65° C., during which process a clear solution forms. In the next step, 0.5 ml of 20% strength potassium thiocyanate solution and 15% of the N-oxide solution prepared are introduced into a reaction vessel at 40° C. Then, N-oxide is added dropwise in such a manner that the molar amount of $CO_2$ formed corresponds to approximately 70% of the molar amount of N-oxide which has been added dropwise. For example, 2 l of $CO_2$ have formed after a total of 30% of the N-oxide solution has been run in. This procedure prevents the accumulation of N-oxide in the solution. If the rate of the $CO_2$ evolution slows down, potassium thiocyanate solution is added in such a way that the amount of $CO_2$ formed again corresponds to approximately 70% of the N-oxide which has been added dropwise. In this manner, $CO_2$ is evolved continuously. After all the N-oxide solution and 4.5 ml of potassium thiocyanate solution have been added dropwise in the course of 1.5 hours, an evolution of gas can no longer be observed after a further 15 minutes. In total, 4.6 l of $CO_2$ have formed. The solution is cooled to room temperature and the precipitate which has separated out is filtered off with suction and dried. 35.5 g of pure N-phosphonomethylglycine are isolated, which corresponds to a yield of 80% based on the amount of N-phosphonomethyliminodiacetic acid employed.

EXAMPLE 3

37 g of N-phosphonomethyliminodiacetic acid and 0.72 g of ammonium molybdate tetrahydrate are suspended in 40 ml of water and the suspension is warmed to 55° C. 11.6 g of 50% strength hydrogen peroxide solution are subsequently added dropwise and stirring is continued for 1.5 hours at 65° C., during which process a clear N-oxide solution forms. In the next step, 0.5 ml of the mother liquor of Example 2 and 15 ml of the N-oxide solution which has been prepared are introduced into a reaction vessel, and N-oxide solution is subsequently added dropwise. When $CO_2$ is no longer formed, more mother liquor is added in 1-ml portions. After all of the N-oxide solution and 22 ml of mother liquor have been added dropwise and an evolution of gas can subsequently no longer be observed, the solution is cooled. The precipitate which has separated out is filtered off with suction and dried. 23.5 g of pure N-phosphonomethylglycine are isolated, which corresponds to a yield of 85% based on the amount of N-phosphonomethyliminodiacetic acid employed.

EXAMPLE 4

190 g of N-phosphonomethyliminodiadetic, acid and 4.2 g of ammonium molybdate tetrahydrate are suspended in 300 ml of water. 66 g of 50% strength hydrogen peroxide solution are added dropwise at 65° C. in the course of one hour and stirring is subsequently continued for 45 minutes at 65° C., during which process a clear solution forms. In the course of 2 hours, this N-oxide solution is added dropwise at 40° C. to 0.64 g of ammonium thiocyanate in 100 ml of water, during which process gas is evolved continuously. A colorless precipitate separates out even while N-oxide is still being metered in. In total, 17.1 l of gas are formed during the fragmentation. The reaction mixture is subsequently cooled to 10° C. and the precipitate which has formed is filtered off with suction and dried. 110.6 g of N-phosphonomethylglycin are isolated in a purity of 99%. A second precipitation in the mother liquor yields a further 11.1 g of pure N-phosphonomethylglycine. Thus, a total yield of 85% is obtained, based on the amount of N-phosphonomethyliminodiacetic acid employed.

Figure 2:
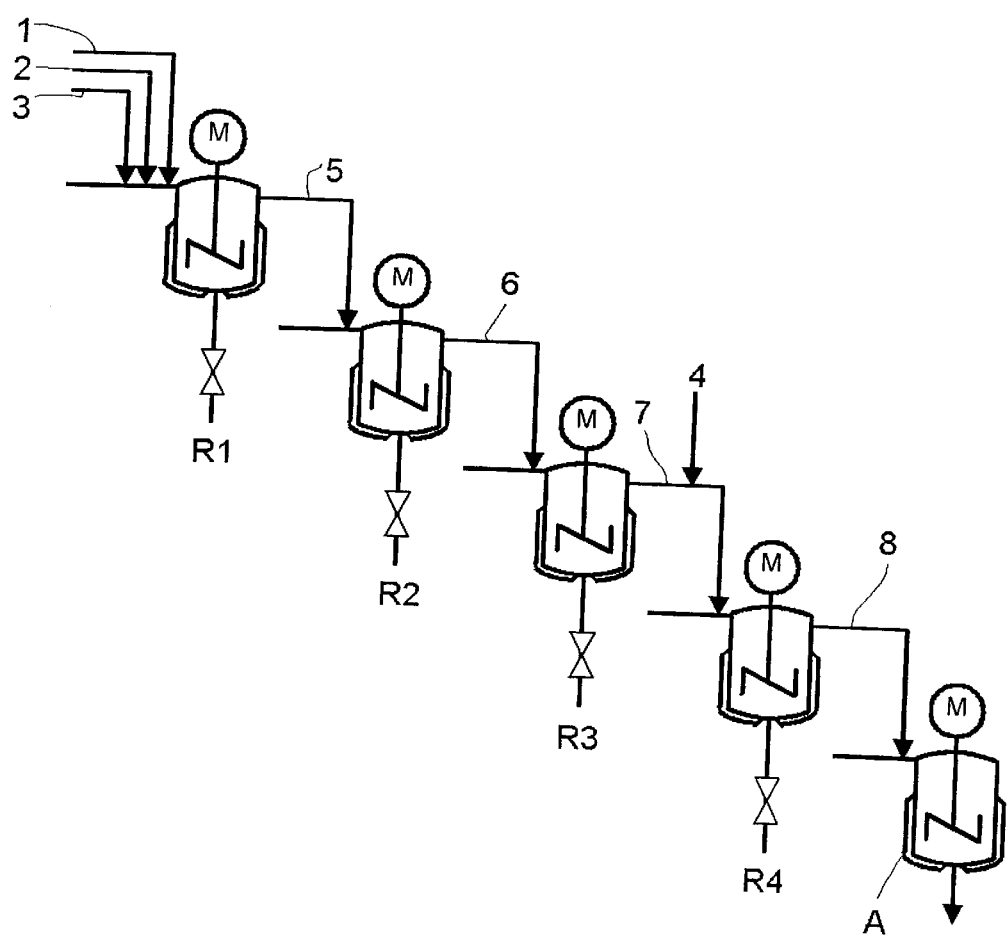
FIG. 2 is a schematic representation of apparatus for carrying out the process for the preparation of phosphonomethylglycine representing a cascade of four stirred reactors (R1, R2, R3 and R4) connected in series and a thermostatted discharge vessel A.

In Examples 5 and 6 below, the process according to the invention is illustrated on a semi-industrial and industrial scale with reference to FIGS. 1 and 2. The figures show a schematic apparatus for carrying out the process, parts which are not essential for the process having been omitted.

EXAMPLE 5

A cascade of stirred reactors (cf. FIG. 1) composed of two heatable and coolable stirred vessels with a reaction volume of 1.0 $dm^3$ (R1) and 2.0 $dm^3$ (R2) connected in series and a thermostatted discharge vessel A was charged as follows:

| Stream | Feedstock | Quantity [g/h] | Form |
|--------|-----------|----------------|------|
| (1) | PMIDA[1] | 163 | suspension |
|  | $H_2O$ | 375 | (30% strength) |
| (2) | $(NH_4)_6Mo_7O_{24} \times 4\ H_2O$ | 3.2 | solution |
|  | $H_2O$ | 12.8 | (20% strength) |
| (3) | $H_2O_2$ | 24.6 | solution |
|  | $H_2O$ | 24.6 | (50% strength) |
| (4) | $NH_4SCN$ | 0.7 | solution |
|  | $H_2O$ | 6.5 | (10% strength) |

[1]Phosphonomethyliminodiacetic acid

Streams (1), (2) and (3) were pumped continuously into the first reactor R1 at 65.0±1.0° C. Via an overflow 5, the resulting, virtually clear solution of the phosphonomethyliminodiacetic acid N-oxide traveled into reactor R2, into which stream 4 was pumped at 32.0±2.0° C., equally continuously. From there, the resulting suspension which contained glyphosate as product of interest traveled via overflow 6 into the discharge vessel A, which was held at 5° C. and was emptied hourly. The solid contained in the discharge was filtered off, washed with a little water and dried at 40° C. On average, 91.1 g/h of glyphosate formed in a purity of >90% (HPLC).

EXAMPLE 6

A cascade of stirred reactors (cf. FIG. 2) composed of four heatable and coolable stirred vessels R1, R2, R3 and R4 with a reaction volume of 700 l each which were connected in series and a discharge vessel A was charged as follows:

| Stream | Feedstock | Quantity [kg/h] | Form |
|---|---|---|---|
| (1) | PMIDA | 102.2 | suspension |
|  | $H_2O$ | 280.6 | (27% strength) |
| (2) | $(NH_4)_6Mo_7O_{24} \times 4\ H_2O$ | 2.2 | solution |
|  | $H_2O$ | 8.8 | (20% strength) |
| (3) | $H_2O_2$ | 17.6 | solution |
|  | $H_2O$ | 17.6 | (50% strength) |
| (4) | $NH_4SCN$ | 0.3 | solution |
|  | $H_2O$ | 3.1 | (10% strength) |

Streams (1), (2) and (3) were pumped continuously at 65.0±1.0° C. into the first reactor R1. Via an overflow 5, the resulting reaction mixture traveled into a secondary reactor R2 which was held at the same temperature. In a third reactor R3, stream 4 was pumped continuously to the virtually clear solution of the phosphonomethyliminodiacetic acid N-oxide which traveled from R2 via overflow 6. From this third reactor R3, the suspension which formed which contained glyphosate as product of interest traveled via overflows 7 and 8 via a further secondary reactor R4 to a discharge vessel A which was held at a temperature of 5° C. and was emptied hourly. The solid contained in the discharge was filtered off, washed with a little water and dried at 40° C. On average, 64.2 kg/h of glyphosate formed in a purity of >90%, according to HPLC (conversion rate: >99%, yield: 76%).

We claim:

1. A process for the preparation of N-phosphonomethylglycine, wherein N-phosphonomethyliminodiacetic acid N-oxide is brought into contact with a catalytically effective amount of thiocyanic acid or a salt thereof.

2. A process as claimed in claim 1, wherein the N-phosphonomethyliminodiacetic acid N-oxide is brought into contact with ammonium thiocyanate or an alkali metal salt of thiocyanic acid.

3. A method as claimed in claim 1, wherein a cocatalyst is additionally employed.

4. A method as claimed in claim 3, wherein the cocatalyst employed is a water-soluble molybdenum compound, in particular ammonium molybdate or an alkali metal molybdate.

5. A process as claimed in claim 1, wherein the reaction is carried out at a temperature in the range of 10° C. to 100° C.

6. A process as claimed in claim 1, wherein the N-phosphonomethyliminodiacetic acid N-oxide is prepared by oxidizing N-phosphonomethyliminodiacetic acid.

7. A process as claimed in claim 6, wherein the oxidation is carried out with a peroxide compound.

8. A process as claimed in claim 7, wherein the oxidation is carried out in the presence of a catalyst, in particular a water-soluble molybdenum compound.

9. A process as claimed in claim 8, wherein the same catalyst is used as the catalyst for oxidizing the N-phosphonomethyliminodiacetic acid and as cocatalyst for converting the N-oxide.

10. A process as claimed in claim 1, wherein N-phosphonomethyliminodiacetic acid is oxidized with a peroxide compound in the presence of a catalytically effective amount of a water-soluble molybdenum compound to give N-phosphonomethyliminodiacetic acid N-oxide and the reaction mixture is subsequently brought into contact with thiocyanic acid or a salt thereof.

11. The method of claim 4, wherein the catalyst is ammonium molybdate or an alkali metal molybdate.

* * * * *

UNITED STATES PATENT AND TRADEMARK OFFICE
CERTIFICATE OF CORRECTION

PATENT NO.    : 6,696,602 B1
DATED         : February 24, 2004
INVENTOR(S)   : Aust et al.

It is certified that error appears in the above-identified patent and that said Letters Patent is hereby corrected as shown below:

Column 8,
Line 12, delete "catalyst, in particular a";
Lines 11-13, delete ", in particular ammonium molybdate or an alkali metal molybdate";
Line 25, after "compound" insert -- catalyst --.

Signed and Sealed this

Sixth Day of July, 2004

JON W. DUDAS
*Acting Director of the United States Patent and Trademark Office*